US011801618B2

(12) United States Patent
Klein

(10) Patent No.: US 11,801,618 B2
(45) Date of Patent: Oct. 31, 2023

(54) METHOD FOR PRODUCING AN IMPLANT FROM A BIOCOMPATIBLE SILICONE

(71) Applicant: NOVATECH SA, La Ciotat (FR)

(72) Inventor: Frank Klein, Berlin (DE)

(73) Assignee: NOVATECH SA, La Ciotat (FR)

( * ) Notice: Subject to any disclaimer, the term of this patent is extended or adjusted under 35 U.S.C. 154(b) by 0 days.

(21) Appl. No.: 17/774,079

(22) PCT Filed: Oct. 30, 2020

(86) PCT No.: PCT/EP2020/080532
§ 371 (c)(1),
(2) Date: May 3, 2022

(87) PCT Pub. No.: WO2021/099091
PCT Pub. Date: May 27, 2021

(65) Prior Publication Data
US 2022/0371229 A1 Nov. 24, 2022

(30) Foreign Application Priority Data
Nov. 22, 2019 (DE) ............ 10 2019 131 618.9

(51) Int. Cl.
| | |
|---|---|
| B29C 33/38 | (2006.01) |
| B33Y 10/00 | (2015.01) |
| B33Y 80/00 | (2015.01) |
| B29C 64/124 | (2017.01) |
| B29C 64/35 | (2017.01) |
| B33Y 40/20 | (2020.01) |
| A61F 2/04 | (2013.01) |
| B29C 33/56 | (2006.01) |
| B29C 39/00 | (2006.01) |
| B29C 39/38 | (2006.01) |
| B29K 83/00 | (2006.01) |
| B29L 31/00 | (2006.01) |

(52) U.S. Cl.
CPC ............ B29C 33/3842 (2013.01); A61F 2/04 (2013.01); B29C 33/3835 (2013.01); B29C 33/56 (2013.01); B29C 39/003 (2013.01); B29C 39/38 (2013.01); B29C 64/124 (2017.08); B29C 64/35 (2017.08); B33Y 10/00 (2014.12); B33Y 40/20 (2020.01); B33Y 80/00 (2014.12); A61F 2002/043 (2013.01); A61F 2002/046 (2013.01); A61F 2240/004 (2013.01); B29K 2083/00 (2013.01); B29L 2031/7532 (2013.01)

(58) Field of Classification Search
CPC .... A61F 2/04; B29C 33/3835; B29C 33/3842
See application file for complete search history.

(56) References Cited

U.S. PATENT DOCUMENTS

2006/0204699 A1   9/2006   Maltezos et al.

FOREIGN PATENT DOCUMENTS

| CN | 105616043 | 6/2016 |
|---|---|---|
| CN | 106414015 | 2/2017 |
| CN | 107296669 | 10/2017 |
| CN | 108908816 | 11/2018 |
| CN | 109908409 | 6/2019 |
| JP | 2016-28876 | 3/2016 |
| KR | 10-1327313 | 11/2013 |
| WO | WO 2004/026178 | 4/2004 |

OTHER PUBLICATIONS

L. Sereno et al.: "New advances on tracheal stent manufacturing", in: 6th IFAC Conference on Management and Control of Production and Logistics, Fortaleza/Brazil, Sep. 11-13, 2013.
PCT International Search Report dated Jan. 27, 2021 corresponding to PCT International Application No. PCT/EP2020/080532.
Chinese Search Report dated Sep. 11, 2022 by the Chinese Patent Office in Chinese Application 2020800810341.
Translation of Chinese Search Report dated Sep. 11, 2022 by the Chinese Patent Office in Chinese Application 2020800810341.

Primary Examiner — James Sanders
(74) Attorney, Agent, or Firm — Henry M. Feiereisen LLC

(57) ABSTRACT

In a method for producing an implant from a biocompatible silicone, a 3D mathematical model of an implant to be produced is used to create a 3D model of a casting mold for the implant as a negative. The casting mold is produced from a polymeric material through an additive manufacturing process and coated through vapor deposition of a coating material from the parylene family at least in a region that comes into contact with the biocompatible silicone to be cast. A platinum-catalyzed 2-component thermosetting silicone as the biocompatible silicone for the implant is introduced into a mold cavity of the coated casting mold, with a residence time of the implant in a patient's body of more than 29 days. The casting mold is heated to vulcanize the biocompatible silicone, and after cooling down the vulcanized implant is demolded from the casting mold.

14 Claims, No Drawings

METHOD FOR PRODUCING AN IMPLANT FROM A BIOCOMPATIBLE SILICONE

CROSS-REFERENCES TO RELATED APPLICATIONS

This application is the U.S. National Stage of International Application No. PCT/EP2020/080532, filed Oct. 30, 2020, which designated the United States and has been published as International Publication No. WO 2021/099091 and which claims the priority of German Patent Application, Serial No. 10 2019 131 618.9, filed Nov. 22, 2019, pursuant to 35 U. S. C., 119(a)-(d).

BACKGROUND OF THE INVENTION

The invention relates to a method for the production of an implant from a biocompatible silicone.

The invention relates to a method for the production of an implant from a biocompatible silicone according to the features in patent claim 1.

Depending on the application, the residence time of an implant in the body can range from a few hours to a lifetime. Since, depending on its use, an implant, like e.g. a stent, is in direct contact with body tissue, skin, mucous membranes or body fluids such as blood, saliva or secretions, it is important to make it of a suitable material. The suitability for the corresponding application is evaluated on the basis of DIN EN ISO 10993.

The standard ISO 10993 is a series of ISO standards for the biological evaluation of medical devices. The aim of the standard is to assess the biological evaluation with regard to the compatibility of the materials used with the body. Therefore, not only products but also starting materials for the production of medical devices are examined. In addition to the biological testing, the standard also includes physico-chemical tests and analyses of dissolved materials and substances and prescribes compliance with limit values for substances that can be dissolved out.

It is known that an essential property of silicone elastomers is their very good biological compatibility in humans. Silicones refer to a group of synthetic polymers in which silicon atoms are linked via oxygen atoms to form molecular chains and/or networks. The remaining free valence electrons of the silicon are saturated by residual hydrocarbons (mostly methyl groups). In scientific literature, the terms poly(organo)siloxanes or siloxanes in short are often used instead of silicones.

In medical technology, mainly platinum-catalyzed 2-component heat-curing silicones are used. These are subject to strict quality assurance and are offered as "unrestricted" for indefinite retention in the patient.

For certain long-term implants, like e.g. tracheo-bronchial stents, solely high-molecular-weight, i.e. high-viscosity starting materials, are suitable. These result in high elongation strengths of more than 500% at stresses of 10 MPa. The hardness is at 40 to 90 Shore A. As a result, it is possible to produce vascular supports with high stability and low wall thickness.

Shaping these silicone elastomers into stents is implemented either for highly viscous silicone (HCR High Consistency Rubber) through hot pressing or for liquid silicone LSR (Liquid Silicone Rubber) through injection molding in a heated tool. For stability reasons and to improve heat conduction, the tools are mainly made of metal. Vulcanization takes place at 120° C. to 180° C. for about 10 s per mm wall thickness. A higher temperature reduces the vulcanization time.

Previous tracheo-bronchial stents made of silicone are established as serial products in medicine. However, there are a number of patients who, for certain anatomical or medical reasons, cannot be treated with a series product, but who are dependent on an individual vascular support that is available on short notice. When the quantity is one, manufacturing via so-called additive processes theoretically lends itself to this, since these processes enable direct shaping and because of the absence of any tooling costs.

However, direct 3D printing of LSR compound via so-called paste extruders results in low-resolution products. The components A and B of the LSR compound are usually mixed under pressure in a static mixing tube directly before discharge and deposited by a triaxial computer-controlled portal. The high viscosity prevents fine resolution during printing. The individual layers are clearly visible in the lower mm range. In this case, vulcanization takes place layer by layer through heat input via hot air or IR radiation.

A direct 3D printing of UV-curable liquid silicones by stereolithography (SLA) is not possible because the viscosity is too high. Available UV-curable low-viscosity silicones are not biocompatible or do not simultaneously exhibit the required mechanical characteristics to make them suitable for 3D printing. Furthermore, theoretical consideration of silicone chemistry reveals a contradiction between viscosity and mechanical properties. Polysiloxanes with low viscosity in the non-crosslinked state simultaneously possess low mechanical properties in the crosslinked state due to the shorter prepolymers.

Therefore, it is not possible to use additive manufacturing to produce a biocompatible medically suitable and mechanically stressable implant from silicone which implant has high surface quality and can be produced economically in a batch size of one.

The state of the art includes the publication Sereno, L. et al, "New advances on tracheal stent manufacturing", 6th IFAC Conference on Management and Control of Production and Logistics, The International Federation of Automatic Control, Sep. 11-13; 2013 Fortaleza, Brazil, p. 344-349. Various production processes for producing silicone stents from biocompatible silicones are disclosed. A molding tool was produced from ABS material through additive manufacturing. Injected silicone was vulcanized at 180° C. for 5 minutes. No further investigations were carried out with respect to determine whether biocompatibility or chemical purity of the implant was maintained even after contact with the ABS material.

The invention is therefore based on the object to provide a method for the production of biocompatible, medically suitable, mechanically stressable implants with high surface quality from silicone, wherein the method is economically more favorable than known production methods, even for very small quantities.

SUMMARY OF THE INVENTION

This object is attained by a method as set forth hereinafter. Advantageous refinements of the invention are set forth in the subclaims.

The method according to the invention for the production of an implant, in particular a long-term implant, from biocompatible silicone is carried out with the following steps:

a) A mathematical 3-D model of an implant to be produced is provided;
b) Using the 3D model of the implant, a 3D model of a casting mold for the implant is created as a negative;
c) The casting mold is manufactured from a polymeric material through an additive manufacturing process;
d) The casting mold is coated at least in regions that come into contact with the silicone to be cast;
e) The coating is applied through vapor deposition of a coating material from the parylene family;
f) The biocompatible silicone is introduced into the mold cavity of the coated casting mold;
g) The casting mold is heated so that the silicone vulcanizes;
h) The vulcanized implant is demolded from the casting mold after cooling.

The implant involves in particular a long-term implant. The term long-term also relates to a residence time in the body of more than 29 days. The implant is in particular a stent.

The method according to the invention uses indirect 3D printing. In indirect 3D printing, it is not the component, i.e. the implant, that is additively manufactured, but a casting mold with which the implant can be formed. The limitation of the 3D printing process is that a process and material has to be found that has sufficient stability to mold suitable silicones and at the same time has a high printing resolution to produce smooth surfaces and which can also withstand the temperatures used to vulcanize the silicone for a certain time. Furthermore, no ingredients may migrate from the casting mold into the implant during the shaping process and vulcanization. Finally, it must be possible to demold the vulcanized implant after vulcanization without being damaged by excessive forces.

The method according to the invention is based on the fact that initially provision is made for a mathematical 3D model of an implant to be produced. The 3D model represents the input informations of the method according to the invention. In particular, the 3D model can be derived from a biological volume model of the stent previously having been gained from imaging data, like e.g. computed tomography or magnetic resonance imaging, or other 3D data, like e.g. from a 3D scan.

The contours for the solid model, particularly a stent, gained from the imaging data can be modified to achieve a therapeutic effect. For this purpose, medical expertise is applied to ensure that the desired therapeutic effect can be achieved without producing negative side effects, e.g. necrosis.

The method for the production of the implant in accordance with the invention refers to the production process per se starting from the already available data of the implant to be manufactured, regardless of whether and how these data have been previously gained, modified or processed.

Starting from the 3D model of the implant, i.e. starting from the positive mold of the implant, a virtual negative mold is created in the form of a 3D model of a casting mold for the implant. The casting mold can be single-part or multi-part to allow demolding of the finished implant. The casting mold includes a mold cavity for the implant to be produced. The mold cavity is provided with the connections required for casting silicone, e.g. a sprue or riser.

The actual casting mold is produced through an additive manufacturing process, i.e. by a so-called 3D printing process, like e.g. stereolithography or the so-called material jetting. Printing can be implemented with a relatively low layer thickness, so that a high print resolution and a very good surface finish can be achieved, which is essential for medical applications and in particular for the implants involved here. The layer thickness for additive manufacturing should be a maximum of 50 μm and better not exceed 25 μm. A sufficiently temperature-stable print resin should be used as the material for the casting mold. In particular, the print resin should be subsequently post-curable in order to achieve the thermal stability required for vulcanizing the silicone and further in order to be able to meet the mechanical properties of the casting molds. The invention enables the casting mold to be made from polymers that are non-biocompatible. Provided that biocompatible polymers are available, the method according to the invention also makes it possible to use biocompatible polymers for the casting mold.

The casting mold of a polymeric material is coated. The coating is intended to prevent ingredients from migrating from the casting mold into the silicone or implant during the shaping process or during vulcanization. Therefore, at least the regions that come into contact with the silicone to be cast are coated, but in particular the entire casting mold. A diffusion barrier should therefore be created to enable use of non-biocompatible materials for the casting mold in the first place and therefore paves the way for additive manufacturing processes.

The coating is applied through vapor deposition, i.e., using a CVD process. Polymers from the parylene family have proven suitable as coating materials. Parylenes designate a group of inert, hydrophobic, optically transparent polymeric coating materials. CVD deposition of parylenes essentially involves evaporation of a prepolymer (dimer) under vacuum, subsequent pyrolysis of the evaporated dimer to monomers, and finally condensation and polymerization of the coating (parylene) on the cold surface of the casting mold. As a result of the gaseous deposition and high gap penetration capability, areas and structures may also be reached and coated which cannot be coated with liquid-based processes, like e.g. sharp edges and tips or narrow and deep gaps. Coating thicknesses of 0.1 to 10 μm can be applied in a single operation. From 0.6 μm coating thickness, the coatings are free of micropores and pinholes. Coating also has the advantage that the surface of the casting mold is smoothed in the coated regions. Preferably, the coating is in a range greater than 1 μm and preferably in a range from 1 to 10 μm, in particular in a range from 3 to 7 μm.

After coating, the casting mold is prepared to the extent that the biocompatible silicone can be introduced into the mold cavity of the coated mold. This is preferably implemented under pressure via a sprue. In this case, an injection molding process is involved using indirect 3D printing. The silicone must then be crosslinked, i.e. vulcanized. For this purpose, the casting mold is heated. After cooling, the vulcanized implant is demolded from the casting mold and transferred for further use.

Preferably, this method is used to produce a stent, in particular a tracheo-bronchial stent, as an implant. The production is also economically advantageous when such a custom-made tracheo-bronchial stent is produced in quantity one. There is no need to produce a complex metal injection mold, which would result in significant costs for small quantities.

Since tracheo-bronchial stents exist as series components, design knowledge of the series components is available, which also already takes into account the therapeutic effects and is designed in such a way that as few negative side effects as possible are produced. In the method according to the invention, this known information can be used so that the 3D model of the implant can be placed in a CAD system as a negative in a virtual block, i.e., a casting mold, and can be extracted via Boolean operations. The cavity thus created in the block is the later mold cavity. The block is then designed, in particular in several parts, in order to be able to remove the cast implant from the later casting mold. For this purpose, the casting mold can have at least a first half mold, at least a second half mold and at least a core, with all of these components being manufactured additively in the method according to the invention. In addition, there are the modules typical of injection molding, such as sprue, vents, and further functional surfaces, like e.g. centering and fixing of the mold parts to one another.

The individual components of the casting mold constructed in this way are exported from a CAD system in a stereolithographic file format and prepared for 3D printing in a slicer software suitable for the intended 3D printing. During this stage, possible shrinkage of the components can also be taken into account as allowance.

In particular, a UV-curable resin is used as the material for the casting mold. The use of a UV-curable resin makes it possible to give the casting mold the necessary dimensional stability and also the thermal stability for subsequent vulcanization. Depending on the manufacturers specifications for the UV-curable resin, UV curing (post-curing) can be performed in several stages to ensure the thermal stability of the casting mold. For example, UV curing of the casting mold or part of the casting mold may be performed in at least three stages, with a first stage at a temperature of not less than 60° C. for a holding time of at least 60 minutes. This is followed by a second stage at a temperature of not less than 80° C. for a holding time of at least 60 minutes, and finally a third stage at a temperature of not less than 120° C. for a holding time of at least 120 minutes. Prior to curing, the 3D-printed components are freed from support materials typical for printing and cleaned. Cleaning can be implemented in particular by washing in isopropanol for at least 10 minutes and subsequent drying. Post-curing then begins under UV radiation and heat.

Preferably, the casting mold thus produced is cleaned by a plasma cleaning process before further processing. Oxygen plasma etching may find application here and also increases adhesion of the parylene at the same time. For example, the casting mold can be cleaned in a vacuum for at least 3 minutes with an oxygen plasma.

A further pretreatment can be carried out by silanizing. Silanization is also known as the silicoater process. Preferably, silane groups are deposited by a so-called precursor in a vacuum process. A liquid silane is hereby evaporated and deposited on the surface of the component through condensation, thus creating an adhesive base.

The actual coating is subsequently applied, using a polymer from the parylene family for this. In particular, parylene C is deposited via the CVD process. Preferably, the thickness of the parylene C layer is at least 1 µm, in particular at least 5 µm. Preferably, the layer thickness is in a range between 1 and 10 µm. Parylenes have the property that they are diffusion-tight. They form a closed-pore film. According to the invention, the diffusion barrier and the closed-pored structure make it possible to manufacture implants from silicone into which no harmful substances diffuse from the casting mold. Parylene C has the necessary physical properties and exhibits extremely low permeability to moisture and gases.

The casting mold coated in this way is then inspected before further processing, optionally cleaned again, and parts of the casting mold are assembled to form the finished casting mold. The multi-part casting mold can be assembled, for example, by bolting the parts of the casting mold together, thereby closing the mold cavity in a pressure-tight manner in the relevant shaping regions. Closing of the mold cavity or joining of the half molds can be implemented via screws. It is also conceivable to clamp the half molds together, for example in a press.

Subsequently, implantable medical silicone mixed under pressure, in particular medically approved platinum-catalyzed 2K silicone is used, e.g. NuSil™ MED 4870 (NuSil™ is a registered trademark of NuSii Technology, LLC) is introduced into the mold cavity of the casting mold. Introduction of the silicone, in particular injection under pressure, may also be implemented in a preheated tool. The filling process is complete when silicone begins to escape from at least one vent connected to the mold cavity. The silicone thus introduced is then vulcanized, in particular at 120° C. to 180° C. for 10 seconds per millimeter of wall thickness of the implant. Preferably, the casting mold, or the cavity formed by the casting mold, is heated to a temperature of at least 140° C. for at least 10 seconds per millimeter of wall thickness of the implant. For this purpose, the entire casting mold can be placed in an oven and heated at 140° C. until the temperature in the interior is 140° C. The temperature in the mold cavity can be measured by at least one temperature sensor arranged in the at least one core. Since the core is surrounded by the workpiece, the temperature in the core allows a conclusion to be made about the temperature in the mold cavity. The preferred wall thickness range for stents is 0.5 mm to 3 mm.

Heating the casting mold to vulcanize the silicone can be implemented using hot air and/or IR radiation. It is crucial that vulcanization takes place until all of the silicone, i.e. all of the thickness ranges, have been vulcanized.

The casting mold is opened after cooling so that the implant can be demolded. The silicone component can then undergo mechanical aftertreatment, like e.g. by removing sprue cones, risers, adhering webs and other unwanted portions of the implant. The implant can then be cleaned and optionally coated, for example by dip coating, to achieve the desired surface quality. The shaping manufacturing steps of the implant are now complete.

For further use, the implant is preferably packaged in a suitable heat-sealable film that permits sterilization and precludes contamination. In particular, a pouch made of TYVEK™ (TYVEK is a registered trademark of E.I. Du Pont de Nemours and Co.) is involved for this purpose, into which the implant is packaged and heat-sealed. This is followed by a sterilization process, wherein the sterilization can be carried out e.g. by using steam, ETO or hydrogen peroxide plasma.

The method according to the invention enables production of biocompatible, medically suitable and mechanically stressable implants having high surface quality from silicone and producible economically more favorably than with other known production processes, even in very small quantities. In particular, it is possible to use the technology of stereolithography or material jetting without compromising biocompatibility. The involved implants meet the requirements of physicochemical tests and analyses of solutes and substances according to the ISO 10993 standard and comply with limits of substances that can be dissolved out. A process and the use of materials that provide sufficient stability for molding liquid silicones have been demonstrated. The finished product has a smooth surface as a result of the high printing resolution, and surface irregularities have been further reduced by subsequent CVD coatings using a parylene. In addition, the coatings prevent migration of ingredients from the casting mold into the component, so that the involved standard can be met.

The invention claimed is:

1. A method for producing an implant from a biocompatible silicone, said method comprising:
providing a 3D mathematical model of an implant to be produced;
using the 3D mathematical model of the implant to create a 3D model of a casting mold for the implant as a negative;
producing the casting mold from a UV-curable resin through an additive manufacturing process;
cleaning the casting mold, and UV-curing the casting mold in at least three stages, with a first stage in which a temperature of not less than 60° C. is set for a holding time of at least 60 min, with a subsequent second stage in which a temperature of not less than 80° C. is set for a holding time of at least 60 min, and with a subsequent third stage in which as temperature of not less than 120° C. is set for a holding time of at least 120 min;
coating the casting mold through vapor deposition of a coating material from the parylene family at least in a region that comes into contact with the biocompatible silicone to be cast;
introducing into a mold cavity of the coated casting mold a platinum-catalyzed 2-component thermosetting silicone as the biocompatible silicone for the implant;
heating the casting mold to vulcanize the biocompatible silicone;
allowing the vulcanized implant to cool down; and
demolding the vulcanized implant from the casting mold after cooling down.

2. The method of claim 1, further comprising making the casting mold of a non-biocompatible material.

3. The method of claim 1, wherein the implant is a stent, in particular a tracheo-bronchial stent.

4. The method of claim 1, wherein the 3D model for the casting mold is designed in multiple parts to enable removal of the cast implant from the casting mold.

5. The method of claim 4, wherein the additive manufacturing process to produce the casting mold includes additively manufacturing as the multiple parts a first half mold, a second half mold, and a core.

6. The method of claim 1, further comprising cleaning the casting mold by a plasma cleaning process before the casting mold is coated.

7. The method of claim 1, further comprising before being coated through the vapor deposition, cleaning the casting mold and silanizing the cleaned casting mold.

8. The method of claim 1, wherein the casting mold is coated with the coating material at a thickness of at least 1 µm.

9. The method of claim 1, wherein vulcanization of the biocompatible silicone is carried out at 120° C. to 180° C. for of a minimum of 10 sec per mm wall thickness of the implant.

10. The method of claim 1, further comprising, after the biocompatible silicone has been introduced into the casting mold, the casting mold is heated until a temperature of at least 140 QC is reached in a mold cavity of the casting mold for a minimum of 10 sec per mm of wall thickness of the implant.

11. The method of claim 10, wherein the 3D model for the casting mold is additively manufactured in multiple parts including a first half mold, a second half mold, and a core, and further comprising measuring the temperature in the mold cavity via a temperature sensor arranged in the core.

12. The method of claim 1, wherein the casting mold is heated for vulcanizing the biocompatible silicone by means of hot air and/or IR radiation.

13. The method of claim 1, further comprising placing the demolded implant in a heat-sealable film which permits sterilization and precludes contamination.

14. The method of claim 1, further comprising sterilizing the demolded implant by means of steam, ETO or H2O2 plasma.

* * * * *

UNITED STATES PATENT AND TRADEMARK OFFICE
CERTIFICATE OF CORRECTION

PATENT NO. : 11,801,618 B2
APPLICATION NO. : 17/774079
DATED : October 31, 2023
INVENTOR(S) : Frank Klein It is certified that error appears in the above-identified patent and that said Letters Patent is hereby corrected as shown below:

In the Specification

Column 1: Delete Lines 19-21.

Column 4, Line 4: replace "Involved" with -- involved --.

Column 6, Line 10: replace "Nusii Technology" with -- Nusil Technology --.

Signed and Sealed this
Twenty-third Day of April, 2024

Katherine Kelly Vidal
*Director of the United States Patent and Trademark Office*